United States Patent
Yuyama et al.

(10) Patent No.: US 8,494,870 B2
(45) Date of Patent: Jul. 23, 2013

(54) SYSTEM FOR SUPPORTING MEDICINE FILLING OPERATION

(75) Inventors: Hiroyuki Yuyama, Osaka (JP); Kiyoyuki Nakata, Osaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 677 days.

(21) Appl. No.: 11/887,029

(22) PCT Filed: Mar. 29, 2006

(86) PCT No.: PCT/JP2006/306499
§ 371 (c)(1),
(2), (4) Date: Apr. 21, 2009

(87) PCT Pub. No.: WO2006/106749
PCT Pub. Date: Oct. 12, 2006

(65) Prior Publication Data
US 2009/0204255 A1    Aug. 13, 2009

(30) Foreign Application Priority Data
Mar. 30, 2005    (JP) ................................ 2005-096913

(51) Int. Cl.
*G06Q 50/00*    (2012.01)
(52) U.S. Cl.
USPC .............................................. 705/2; 700/216
(58) Field of Classification Search
USPC ............. 221/211, 222, 289; 705/2, 3; 24/297; 235/375
See application file for complete search history.

(56) References Cited

U.S. PATENT DOCUMENTS

| 5,337,919 A | 8/1994 | Spaulding et al. |
| 5,671,592 A | 9/1997 | Yuyama et al. |
| 5,720,154 A | 2/1998 | Lasher et al. |
| 5,771,657 A | 6/1998 | Lasher et al. |
| 5,930,145 A | 7/1999 | Yuyama et al. |
| 5,963,453 A * | 10/1999 | East .............................. 700/244 |
| 6,006,946 A | 12/1999 | Williams et al. |
| 6,119,737 A | 9/2000 | Yuyama et al. |

(Continued)

FOREIGN PATENT DOCUMENTS

| EP | 1 433 457 A1 | 6/2004 |
| JP | 02-083186 | 3/1990 |

(Continued)

OTHER PUBLICATIONS

U.S. Appl. No. 12/729,850, filed Mar. 23, 2010, Yuyama et al.

(Continued)

*Primary Examiner* — Gerald J. O'Connor
*Assistant Examiner* — Jonathan K Ng
(74) *Attorney, Agent, or Firm* — Patterson Thuente Pedersen, P.A.

(57) ABSTRACT

Provided is a system for supporting medicine filling operation determines whether or not a combination of a medicine container and a medicine is appropriate and performs filling operation reliably and quickly without making a mistake. A control means (7) determines whether or not a medicine and a mounting object conform to each other based on medicine identification information or mounting objects identification information received by a communication means (6) and based on a medicine master, mounting master, and exchange table stored in a storage means (4). Information on the medicine, information on the mounting objects, or determination result that is read by the control means (7) and received via the communication means (6) and communication section (10) can be displayed on a display section (9) of a portable terminal (3).

8 Claims, 10 Drawing Sheets

U.S. PATENT DOCUMENTS

| | | | |
|---|---|---|---|
| 6,202,923 B1* | 3/2001 | Boyer et al. ............... 235/375 |
| 6,349,848 B1 | 2/2002 | Uema et al. | |
| 6,625,952 B1 | 9/2003 | Chudy et al. | |
| 6,644,504 B2 | 11/2003 | Yuyama et al. | |
| 6,684,126 B2* | 1/2004 | Omura et al. ................. 700/231 |
| 6,739,476 B2 | 5/2004 | Shigeyama et al. | |
| 6,742,671 B2 | 6/2004 | Hebron et al. | |
| 6,748,295 B2 | 6/2004 | Tilles et al. | |
| 7,080,755 B2 | 7/2006 | Handfield et al. | |
| 7,086,650 B2 | 8/2006 | Fujiwara et al. | |
| 7,234,609 B2 | 6/2007 | DeLazzer et al. | |
| 7,263,411 B2 | 8/2007 | Shows et al. | |
| 7,434,704 B2* | 10/2008 | Yuyama et al. ............... 221/222 |
| 7,562,791 B2 | 7/2009 | Yuyama et al. | |
| 7,630,908 B1* | 12/2009 | Amrien et al. ................. 705/3 |
| 7,801,642 B2* | 9/2010 | Ansari et al. .................. 700/240 |
| 7,861,492 B2 | 1/2011 | Yuyama et al. | |
| 2002/0143429 A1* | 10/2002 | Yuyama et al. ............... 700/216 |
| 2003/0074868 A1* | 4/2003 | Yasuoka et al. ................ 53/493 |
| 2003/0187692 A1 | 10/2003 | Park | |
| 2004/0017475 A1* | 1/2004 | Akers et al. .................. 348/207.1 |
| 2004/0039481 A1* | 2/2004 | de la Huerga ................. 700/236 |
| 2004/0045977 A1* | 3/2004 | William et al. ................ 221/289 |
| 2004/0134043 A1* | 7/2004 | Uema et al. ..................... 24/297 |
| 2005/0131578 A1 | 6/2005 | Weaver | |
| 2005/0240441 A1 | 10/2005 | Suzuki et al. | |
| 2007/0129911 A1 | 6/2007 | Yuyama et al. | |
| 2007/0150092 A1 | 6/2007 | Ohmura et al. | |
| 2008/0017661 A1* | 1/2008 | Hutchinson et al. .......... 221/211 |
| 2008/0271414 A1 | 11/2008 | Yuyama et al. | |
| 2009/0294467 A1 | 12/2009 | Yuyama et al. | |
| 2010/0175782 A1 | 7/2010 | Yuyama et al. | |

FOREIGN PATENT DOCUMENTS

| | | |
|---|---|---|
| JP | 03-242147 | 10/1991 |
| JP | 06-316312 | 11/1994 |
| JP | 08-007014 | 1/1996 |
| JP | 09-034942 | 2/1997 |
| JP | 10-077107 | 3/1998 |
| JP | 11-070901 | 3/1999 |
| JP | 11-208604 | 8/1999 |
| JP | 2001-306688 | 11/2001 |
| JP | 2002-120913 | 4/2002 |
| JP | 2002-126044 | 5/2002 |
| JP | 2002-514152 | 5/2002 |
| JP | 2002-272812 | 9/2002 |
| JP | 2002-272814 | 9/2002 |
| JP | 2002-370701 | 12/2002 |
| JP | 2003-044940 | 2/2003 |
| JP | 2003-099534 | 4/2003 |
| JP | 2003-118816 | 4/2003 |
| JP | 2003-146414 | 5/2003 |
| JP | 2003-206024 | 7/2003 |
| JP | 2003-237703 | 8/2003 |
| JP | 2003-237711 | 8/2003 |
| JP | 2003-284760 A1 | 10/2003 |
| JP | 2003-530650 | 10/2003 |
| JP | 2004-000429 A | 1/2004 |
| JP | 2004-103001 | 4/2004 |
| JP | 2004-157579 | 6/2004 |
| JP | 2004-187958 | 7/2004 |
| JP | 2004-256242 | 9/2004 |
| JP | 2004-348717 | 12/2004 |
| JP | 2005-122360 | 5/2005 |
| JP | 2005-140763 A | 6/2005 |
| JP | 2005-192702 | 7/2005 |
| WO | WO 99/29467 | 6/1999 |
| WO | WO 01/77927 A1 | 10/2001 |
| WO | WO 2004/014288 | 2/2004 |
| WO | WO 2004/014734 | 2/2004 |

OTHER PUBLICATIONS

U.S. Appl. No. 12/729,850.
International Search Report for International Application No. PCT/JP2006/302152 dated Jun. 13, 2006.
Application and File History of U.S. Appl. No. 12/064,740 filed Jun. 2, 2009, inventors Yuyama et al.
Application and File History of U.S. Appl. No. 11/884,333 filed Aug. 14, 2007, inventors Yuyama et al.
Application and File History of U.S. Appl. No. 12/729,850 filed Mar. 23, 2010, inventors Yuyama et al.
Someda, Kuniyuki, "Management of Diagnosis Materials by Handy Terminal and Personal Computer," vol. 6, No. 4 (1994).

* cited by examiner

FIG. 9

TABLET FILLING

CONDITION SETTING

FILLING DATE  2005/03/10 ▽  ~  2005/03/10 ▽

DISPLAY ORDER   ● ORDER OF DATE   ○ ORDER OF MACHINE NUMBER   ○ ORDER OF MEDICINE CODE

[ERROR EXTRACTION]

FILLING LIST

| JAN CODE | MEDICINE CODE | MEDICINE NAME | MACHINE NUMBER | CASSETTE No. | DATE | FILLING PERSON NAME | ERROR CONTENTS |
|---|---|---|---|---|---|---|---|
| 4987288731252 | ITO01 | ITOROL TABLET 20mg | 02 | D | 2005/03/10 | MANAGER | MEDICINE CODE DOES NOT AGREE |
| 4987288731252 | ITO01 | ITOROL TABLET 20mg | 02 | D | 2005/03/10 | MANAGER | MEDICINE CODE DOES NOT AGREE |
| 4987116060615 | AKA01 | AKARUDII CAPSULE 1.25mg | 02 | 461 | 2005/03/10 | MANAGER | MEDICINE CODE DOES NOT AGREE |
| 4987123122993 | AZA01 | AZANIN TABLETS 50mg | 02 | 471 | 2005/03/10 | MANAGER | MEDICINE CODE DOES NOT AGREE |
| 4987288731252 | ITO01 | ITOROL TABLET 20mg | 01 | 66 | 2005/03/10 | MANAGER | MEDICINE CODE DOES NOT AGREE |
| 4987116060615 | AKA01 | AKARUDII CAPSULE 1.25mg | 02 | 461 | 2005/03/10 | MANAGER | MEDICINE CODE DOES NOT AGREE |

| F1 EXTRACTION | F2 | F3 ERROR EXTRACTION | F4 | F5 | F6 | F7 PRINT | F8 | F9 | F10 END | F11 | F12 |

SET FILLING CONDITION

FIG. 10

TABLET FILLING

CONDITION SETTING

FILLING DATE  2005/03/10 ▽ ~ 2005/03/10 ▽

DISPLAY ORDER: ● ORDER OF DATE  ○ ORDER OF MACHINE NUMBER  ○ ORDER OF MEDICINE CODE

ORDINARY EXTRACTION

FILLING LIST

| JAN CODE | MEDICINE CODE | CLASS | MEDICINE NAME | MACHINE NUMBER | CASSETTE No. | FILLING AMOUNT | FILLING DATE | FILLING PERSON NAME |
|---|---|---|---|---|---|---|---|---|
| 4987288731252 | ITO01 | | ITOROL TABLET 20mg | 02 | 471 | 100 | 2005/03/10 | MANAGER |
| 4987116060615 | AKA01 | | AKARUDII CAPSULE 1.25mg | 01 | 54 | 100 | 2005/03/10 | MANAGER |
| 4987288731252 | ITO01 | | ITOROL TABLET 20mg | 02 | 471 | 100 | 2005/03/10 | MANAGER |
| 4987288731252 | ITO01 | | ITOROL TABLET 20mg | 03 | 471 | 100 | 2005/03/10 | MANAGER |
| 4987288731252 | ITO01 | | ITOROL TABLET 20mg | 02 | 471 | 10 | 2005/03/10 | MANAGER |

| F1 | F2 | F3 | F4 | F5 | F6 | F7 | F8 | F9 | F10 | F11 | F12 |
|---|---|---|---|---|---|---|---|---|---|---|---|
| | EXTRACTION | ERROR EXTRACTION | | | | PRINT | | | END | | |

SET FILLING CONDITION

SYSTEM FOR SUPPORTING MEDICINE FILLING OPERATION

TECHNICAL FIELD

The present invention relates to a system for supporting a medicine filling operation that is used in a filling operation into a device for supplying a medicine such as a tablet or an ampule.

BACKGROUND ART

Conventionally, the following systems have been known as a system for, when a medicine is filled into a medicine container, performing this filling operation quickly and appropriately.

That is, a first system is constructed so that after a filling operation of a medicine into a medicine container has been performed, a wide-area check is carried out to find which position of a medicine preparing equipment this medicine container should be fitted to, thereby making it possible to inform a fitting place (see Patent Document 1, for instance).

Also, a second system is constructed so that when a medicine is filled into a medicine container, registered data is displayed through reading of a barcode provided to the medicine container with a barcode reader, thereby enabling a person preparing a medicine himself/herself to determine whether or not the medicine container is appropriate for the filling of the medicine (see Patent Document 2, for instance).

Patent Document 1: JP 2002-27812 A
Patent Document 2: JP 5-60948 A

DISCLOSURE OF INVENTION

Problems to be Solved by the Invention

In the former system, however, there is provided such a construction that it is merely possible to inform a fitting destination of a medicine container. It is not possible to further determine whether or not a medicine filled into the medicine container is appropriate. It is also assumable that when a medicine filled into a medicine container is different from a medicine filled last time, when a residual of the previous medicine adheres to the newly filled medicine or mixing of the filled medicine occurs, an unexpected happening will occur. Accordingly, a system for filling a specific medicine into a medicine container reliably without making a mistake is desperately desired.

Also, in the latter system, at the time of filling a medicine into a certain medicine container, it is only determined which medicine should be filled through reading of a barcode provided to the medicine container. Whether or not the medicine to be filled is appropriate needs to be determined by a person preparing a medicine himself/herself, which results in a fear that a human mistake will be made.

In particular, when a filling operation of a medicine is distributed among multiple persons and is performed by them, it is impossible to cope with such a situation in either system described above.

Therefore, an object of the present invention is to provide a system for supporting a medicine filling operation, with which it becomes possible to determine whether or not a combination of a medicine container and a medicine is appropriate and perform the filling operation reliably and quickly without making a mistake.

Means for Solving the Problems

In order to solve the above-mentioned problems, the present invention provides a system for supporting a medicine filling operation for filling a medicine into a medicine container, including: a portable terminal including an input section for inputting information for identification of the medicine or information for identification of an object on which the medicine is to be mounted, a display section, and a communication section; a storage means for storing a medicine master composed of information on the medicine associated with the medicine identification information, a mounting master composed of information on the mounting object associated with the mounting object identification information, and an exchange table for associating the medicine information and the mounting object information with each other; a communication means for receiving the medicine identification information or the mounting object identification information inputted with the input section of the portable terminal via the communication section; and a control means for judging whether or not the medicine and the mounting object conform to each other based on the medicine identification information or the mounting object identification information received by the communication means and based on the medicine master, the mounting master, and the exchange table stored in the storage means, in which the display section of the portable terminal can display the medicine information, the mounting object information, or a determination result read by the control means and received via the communication means and the communication section.

With this construction, it becomes possible to, when the medicine identification information or the mounting object identification information has been inputted with the input section of the portable terminal, display the medicine information or the mounting object information stored so as to be associated with the inputted information on the display section. Also, it becomes possible to, when the other remaining one of the information (mounting object identification information or medicine identification information) has been inputted with the input section afterward, determine, at the control means, whether or not the medicine and the mounting object conform to each other and display a result of the determination on the display section.

It should be noted here that the medicine identification information refers to an identification symbol, such as a medicine code, which is unique to the medicine. The mounting object identification information refers to an identification symbol, such as a medicine container number, with which it is possible to identify the medicine container. The medicine information refers to information, such as a medicine name, a medicine code, or efficacy, which concerns the medicine. The mounting object information includes coordinate data for identification of a fitting position of the medicine container. The input section of the portable terminal includes a construction, such as a barcode reader or a transponder, which enables automatic discrimination of the medicine container through reading of a barcode, an IC (Integrated Circuit), or the like provided to the medicine container as well as a construction, such as a physically operable button or the like or a touch panel, which enables manual input.

Preferably, when one of the medicine identification information and the mounting object identification information has been received by the communication means, the control means reads corresponding one of the information based on the medicine master or the mounting master stored in the storage means and reads the other remaining one of the information associated with the read information based on the exchange table; and the medicine information and the mounting object information read by the control means and received via the communication means and the communication section is made displayable on the display section of the portable terminal.

With this construction, when one of the medicine identification information and the mounting object identification information has been inputted with the input section at the portable terminal, not only corresponding information, in other words, one of the medicine information and the mounting object information but also the other remaining one of the information are displayed on the display section. As a result, it becomes possible for a person preparing a medicine to confirm which medicine container should be filled with a certain medicine on the display section merely by inputting the medicine identification information. Also, it becomes possible for the person preparing the medicine to confirm which medicine should be filled into a certain medicine container on the display section merely by inputting the mounting object identification information.

Preferably, the storage means further stores image information concerning the medicine, and the portable terminal further includes an image reading section for, under a state where the medicine information is displayed on the display section, receiving the image information stored in the storage means via the communication section and the communication means and enabling display thereof on the display section.

With this construction, it becomes possible to confirm, at the portable terminal, an actual external appearance of a medicine to be filled and whether or not there is a mistake by comparing an image to an actual thing, so it becomes possible to prevent a filling mistake more reliably.

It should be noted here that it is preferable that the image information includes not only the external appearance of the medicine but also an external appearance under a packaged state and, in short, any information may be adopted as long as the medicine to be filled is identified from the external appearance.

Preferably, the storage means stores the exchange table in which one medicine is associated with a plurality of mounting objects; the control means reads the medicine information or the mounting object information stored on the exchange table in the storage means based on the medicine identification information or the mounting object identification information received via the communication section and the communication means and sends the read information to the communication section of the portable terminal via the communication means; and when the medicine information is displayed on the display section of the portable terminal, a plurality of corresponding mounting objects are displayed together with the medicine information.

With this construction, it becomes possible to, when it is impossible to fill all of a medicine into a certain mounting object, in other words, a medicine container, clearly know which medicine container should be next filled with the remaining medicine, thereby making it possible to perform a filling operation smoothly.

Preferably, the control means calculates a remaining amount of the medicine on each mounting object based on a filling amount of the medicine into the mounting object and a delivery amount of the medicine from the mounting object, determines whether or not filling of the medicine is required based on the calculated remaining amount of the medicine, and displays corresponding mounting object information on the display section of the portable terminal when it has been determined that the filling is required.

With this construction, it becomes possible to identify a medicine container that requires medicine filling with ease, which makes it possible to perform a filling operation more quickly.

Preferably, the control means stores a filling record together with a filling person name in the storage means based on a filling completion signal from the portable terminal.

With this construction, it becomes possible to identify which medicine has been filled into which medicine container by whom afterward, which makes it possible to, even in the event of a filling mistake or the like, find out who is responsible for the mistake or the like without difficulty.

Preferably, when there is an error in information inputted with the input section of the portable terminal, the control means stores an error record in the storage means and causes the display section of the portable terminal to display error information based on the error record.

With this construction, it becomes possible for a person preparing a medicine to identify a cause of an error with ease. In addition, an error record is left, so it becomes possible to find out the cause of the error. For instance, it becomes possible to, when an error that is erroneous picking-up frequently occurs regarding a certain medicine, take various measures such as devising of a display form of medicine information.

The control means may be constructed using a web server.

With this construction, even in the case of multiple portable terminals, it becomes possible to collectively manage the terminals, so it becomes possible to share data with ease. Also, easy installation via the Internet can be carried out. More specifically, it is possible to only install relay equipment (web server) connected to the Internet may be installed along with multiple portable terminals connected to the relay equipment. The relay terminal equipment and the portable terminals may be connected to each other through a wireless LAN or the like.

A system for supporting a medicine filling operation according to claim 8, characterized by that the storage means may be installed at the main server and the web server may be installed in each unit of a plurality of portable terminals that are collectively used.

Effects of the Invention

In the present invention, when one of information (medicine identification information and mounting object identification information) has been inputted, a portable terminal is caused to display information (medicine information or mounting object information) associated with this information, so it becomes possible to check whether or not a medicine to be processed and an object, on which the medicine is to be mounted, are appropriate. Also, it becomes possible to, when the other remaining one of the information (mounting object identification information and medicine identification information) has been inputted afterward, automatically determine whether or not the medicine and the mounting object confirm to each other at the control means. As a result, it becomes possible to perform a medicine filling operation with efficiency without making a mistake.

BEST MODE FOR CARRYING OUT THE INVENTION

Hereinafter, an embodiment of the present invention will be described with reference to the accompanying drawings.

FIG. 1 is a schematic explanatory diagram showing the whole of a system for supporting a medicine filling operation according to this embodiment. This system for supporting a medicine filling operation includes a main server 1, a web server 2, and multiple portable terminals 3.

The main server 1 includes a storage device 4, a display device 5, and the like. In the storage device 4, a medicine master, a mounting master, an exchange table, an image master, a filling history table, an error history table, and the like are stored. The medicine master is composed of medicine information such as medicine codes or medicine names. The mounting master is composed of mounting object information such as (mounting object) numbers assigned to medicine containers (cassettes, in this embodiment) in which medicines (tablets, ampules, or the like) are accommodated by kind. On the exchange table, the medicine information and the mounting object information are associated with each other. The image master is composed of images showing external appearances of each medicine. Here, the image master is composed of photograph data of each of the front surfaces and back surfaces of the medicines themselves. Note that the present invention is not limited to the external appearances of the medicines themselves and photograph data of packages, in which the medicines are accommodated, or the like may be used. In addition, design printed on boxes, in which the medicines are accommodated, or the like can be also used, in short, any image data may be used as long as the image data can identify the medicines. Stored in the filling history table are filling records each of which shows which medicine has been filled into which medicine container by whom. On the error history table, information in a case where an error has occurred as a result of filling check processing performed in a manner described later, in more detail, information that is necessary to perform display as shown in FIG. 9 is stored. The display device 5 is used when the filling records or error histories to be described later are displayed in a list, for instance.

The web server 2 includes a communication device 6, a control device 7, and the like, exchanges data with the storage device 4 of the main server 1 and the multiple portable terminals 3, and carries out filling processing to be described later. In the data exchange with the portable terminals 3, displaying on a display section 9 of each portable terminal 3, collective management of input/output data, and the like are performed.

Each portable terminal 3 includes an input section 8, a display section 9, and a communication section 10. In this embodiment, a PDA (Personal Digital Assistance) is used as the portable terminal 3.

The input section 8 is a section for inputting the medicine identification information and the mounting object information. In this embodiment, the input section is constructed using a barcode reader integrated with a main body of the portable terminal 3. With the barcode reader, it is possible to read a barcode (JAN code) printed on a package (medicine box 11) of a medicine or the like and a barcode (cassette number) given to a cassette 12 accommodating a medicine. In other words, by using the barcode reader, it becomes possible to input the JAN code and the cassette number.

The display section 9 is constructed using a touch panel or the like and displays a result of the input with the input section 8, the medicine information and the mounting object information associated with the inputted information, and the like. When the display section 9 is constructed using a touch panel, it is also possible to provide the function of the input section 8 to the display section 9. In other words, when it becomes possible to directly input numerical values corresponding to the JAN code and the cassette number or the like through an operation of the touch panel, it allows the input even when the barcode reader is out of order, for instance. Note that aside from direct operations of buttons or the like displayed on a screen, a construction is also possible in which buttons or the like that are operable through physical pressing-down are operated.

The communication section 10 is connected to a hub via a wireless LAN and allowed to perform communication with the web server 2 via the communication device 6.

Next, an operation of the system for supporting a medicine filling operation having the construction described above, in other words, filling processing will be described by following flowcharts shown in FIGS. 2 and 3.

If a person has inputted a filling person code and a password and has operated an OK button 13 using the input section 8 of the portable terminal 3 on an initial screen (see FIG. 4) which is initially displayed (step S1), it is determined whether or not the person is someone who has a right to perform a medicine filling operation by referring to a user master (step S2). If an inappropriate input has been made, an error dialog (not shown) is displayed (step S3). If an appropriate input has been made, switching to an operation menu screen shown in FIG. 5 is performed (step S4).

In the operation menu screen, a filling person name and multiple operation selection buttons indicating selectable operations are displayed. In FIG. 5, as the operation selection buttons, a tablet filling button 14 and an injection filling button 15 are displayed. Note that it is possible to increase the selectable operations and, for instance, it is possible to add each of a powdered medicine filling operation, a liquid medicine filling operation, a counting operation, and each medicine filling operation for external use. Here, the tablet filling refers to tablet filling into each tablet cassette fitted to a tablet feeder. At the tablet feeder, each cassette 12 is arranged in various conventionally known forms such as a matrix form and a cylindrical form. For instance, when the cassette 12 is arranged in a matrix manner, it is possible to use XY coordinates as filling object information. Also, the injection filling refers to ampule filling into a medicine container, for instance.

If the tablet filling operation has been selected, a tablet filling screen shown in FIG. 6 is displayed on the display section 9. At the time when the display is switched to this tablet filling, a message "Read JAN cassette barcode" is displayed in an instruction field 16 (note that the instruction field 16 of FIG. 6 is contents displayed in step S5 or later to be described later), thereby informing a person preparing a medicine of an operation that he/she should perform next. In response to the message, the person preparing the medicine reads a barcode (cassette number) provided to each cassette 12 of the tablet feeder or a barcode (JAN code) corresponding to a medicine that should be filled into the cassette 12 with the input section 8 provided to the portable terminal 3, in other words, the barcode reader. As to the JAN code, it is possible to read a barcode given to the medicine box 11 or reading from a barcode list prepared separately is possible. Alternatively, the JAN code may be directly inputted using the operation buttons of the portable terminal 3 or the like.

If one of the barcodes has been read (step S5), medicine information and mounting object information are read by referring to the medicine master or the mounting master and the exchange table in the storage device 4 based on the read cassette number or JAN code (step S6). In other words, in the case of the cassette number, the mounting object information is read from the mounting table and medicine information corresponding to this mounting object information is read by referring to the exchange table. Also, in the case of the JAN code, the medicine information is read from the medicine master and mounting object information corresponding to this medicine information is read by referring to the exchange table.

Then, on the display section 9, the JAN code, a medicine name, and the like are displayed (step S78) and cassette candidates are displayed (step S89). As a result, it becomes possible for the person preparing the medicine to easily identify and find a medicine container, into which a medicine is to be filled, or a medicine, which should be filled, in accordance with display contents.

It should be noted here that the association between the medicine and the mounting object is not limited to the one-to-one relationship and a case where multiple cassettes 12 are associated with a certain medicine, in other words, a one-to-many relationship is also included. In the case of the one-to-many association, priorities may beset. For instance, the priorities may be set based on medicine remaining amounts calculated from filling amounts and delivery amounts so that a less medicine remaining amount is given a higher priority. In FIG. 6, an example is shown in which cassettes 12 that are candidates for an object, on which a medicine (Itorol tablet) is to be mounted, are set at three locations that are a No. 02 machine 471, a No. 03 machine 471, and a No. 04 machine 471. Also, when a medicine filling operation is simultaneously performed at multiple portable terminals 3, it is preferable that each cassette 12 that is already under the filling operation is not displayed or is displayed so that it is possible to find that the cassette 12 is under the filling operation.

If an image display button 17 has been touch-operated in the operation menu screen (step S10), corresponding image data is transferred from an image file and is displayed on the display section 9 (step S11). In this embodiment, as shown in FIG. 7, an image of each of the front and back of a tablet is displayed (note that a filling registration button 18 shown in FIG. 7 is displayed only in a case where the image display button 17 has been operated in the tablet filling screen shown in FIG. 6 in step S12 or later to be described later, so the filling registration button 18 is not displayed in this stage). In this image, it is possible to discriminate a carved seal. Note that displayable image is not limited to the front surface and back surface of a tablet and in the case of a PTP (Press Through Package) medicine, an external appearance of the PTP itself, an external appearance of a package for supply from a pharmaceutical company or the like such as a box in which the medicine is accommodated, or the like are also included. It is sufficient these image data are set to be registered at will. As a registration method, for instance, a construction can be made so that an image photographed with a digital camera or the like is transferred to the storage device 4 of the main server 1. Also, a camera function may be given to the portable terminal 3 and input may be performed at the site of medicine preparation. Further, it is preferable that the displaying on the display section 9 is settable at will in accordance with an operation form. For instance, when a medicine filling operation is performed from a package state, when a package image is displayed, determination is facilitated. In addition, when there is similarity in image data between different medicines, it is also possible to display other different images together or display the different images with higher priorities. For instance, when external appearances of medicines themselves are similar to each other, by displaying images of their packages together, it becomes possible to effectively prevent a mix-up. By adding a function for enabling easy registration of image data in this manner, it becomes possible to, even if a medicine shape, package design, or the like has been changed, cope with this situation with ease on a user side.

Then, a type of the barcode read in step S5 described above is checked (step S11) and if the cassette number has been read, a message "Read JAN barcode" is displayed in the instruction field 16 of the display section 9 (step S12). After the JAN code has been read (step S13), the processing proceeds to the next step. Also, if the JAN code has been read, a message "Read cassette barcode" is displayed (step S14). After the cassette number has been read (step S15), the processing proceeds to the next step. With this construction, it becomes possible for the person preparing the medicine to know what to do next at a glance, which improves workability. Also, when information corresponding to the read barcode does not exist, an error message showing this situation is displayed, thereby calling attention of the person preparing the medicine.

Next, if the other remaining one of the barcodes has been read by the barcode reader (step S12), filling check processing is performed by comparing information associated with information identified with the barcode previously read and information identified with the barcode currently read with each other (step S136). For instance, if a JAN code of a medicine, for which a filling operation is to be performed, has been read, and a cassette number or the like associated with this JAN code has been displayed, a cassette number of a cassette, into which the medicine is to be filled, is read and it is determined whether or not the cassette number previously displayed and the cassette number currently read conform to each other. Also, if the cassette number of the cassette, into which the medicine is to be filled, has been read and a medicine code or the like associated with the cassette number has been displayed, a code of the medicine to be filled is read and it is determined whether or not the medicine code previously displayed and the medicine code currently read conform to each other.

After the barcodes of the medicine and the mounting object have been read and the filling check processing has been performed in this manner, it is determined whether or not the medicine and the mounting object conform to each other based on a result of the check (step S147). When information on them does not conform to each other, a check error display shown in FIG. 8 is performed (step S158). As to the contents of the error display, a message "Read correct medicine JAN code or cassette barcode" may be displayed to thereby urge the person preparing the medicine to perform the operation again, for instance. In this case, after the barcode of the medicine or the cassette has been read again with the barcode reader, information corresponding to the barcode newly read is read from the storage device 4 of the main server 1 and is displayed on the display section 9 and the filling check processing is carried out again.

An error result is stored on the error history table in the storage device 4 of the main server 1 as an error history. It is possible to display, in a list, contents stored on the error history table on the display device 5 of the main server 1. In FIG. 9, a screen, in which the contents are displayed in a list, is shown. In this embodiment, it becomes possible to set an extraction condition and to display extraction results in a list. A filling date (period) is set as the extraction condition and it becomes possible to sort a display order of the list-display by date, machine numbers (device numbers of tablet feeders or the like, for instance), or medicine codes. A list-displaying area is composed of JAN codes, medicine codes, medicine names, cassette numbers, dates (of filling operations), filling person names, and error contents.

Next, if it has been found as a result of the filling check processing that the information on them conform to each other, it is determined whether or not a setting of filling amount input confirmation has been made (step S169). If the filling amount input confirmation has been set, a filling amount input screen is displayed on the display section 9 (step S1720) and information of the mounting master is updated (step S2219) through input of a filling amount using a ten-key pad displayed in the screen (step S1821). Then, the screen is switched to a medicine filling screen shown in FIG. 7 (step S203). On the other hand, if the filling amount input confirmation has not been set, in other words, if a filling amount has been determined in advance, the medicine filling screen is displayed without displaying the filling amount input screen. Processing thereafter is the same.

In the medicine filling screen, a medicine name and an image data related thereto are displayed, so it becomes possible to perform confirmation of appropriateness with reliability even in the case of a similar medicine, which makes it possible to prevent the person preparing the medicine from making a filling mistake. Also, the filling registration button 18 is set operable (step S214). In this situation, if the filling registration button 18 is operated, a filling history is stored on the filling history table (step S225). Also, it is determined whether or not the medicine currently filled is subjected to filling processing into another filling object (cassette) (step S236).

In a case where there is filling processing into another cassette, the processing returns to step S14 described above and the processing described above is repeated. For instance, when it is impossible to fill all of a certain medicine into one cassette, and there is another cassette into which it is possible to fill the medicine, a cassette number thereof and an input urging message are displayed on the display section 9 of the portable terminal 3. On the other hand, when there is no filling processing into another cassette, each field of the medicine filling screen is set under a blank state and it is determined whether or not an end button has been operated (step S27). If the end button has not been operated and a barcode has been read (step S5), the same processing as above is repeated.

When there is another filling processing, the processing returns to step S5 and the screen returns to the medicine filling screen whose each field is set under a blank state. On the other hand, if filling amount input confirmation has not been set, in other words, if a filling amount has been determined in advance, the medicine filling screen is displayed without displaying the filling amount input screen. Processing thereafter is the same.

Finally, the end button is operated (step S24), in response to which the tablet filling processing is ended. A filling record including a filling person name and a filled medicine name is stored on the filling history table in the storage device 4 of the main server 1. It is possible to browse stored results as a list on the display device 5. A screen in which filling records are displayed in a list is shown in FIG. 10. FIG. 10 has the same construction as FIG. 9 except that there is no "error contents" row. Also, it is possible to perform switching between FIGS. 9 and 10 through an operation of a function key provided in a lower area.

Incidentally, at the tablet feeder described above, the number of medicines filled through a filling operation and the number of medicines delivered from the cassette 12 are all stored as a filling record. Consequently, it is possible to manage the number of medicines remaining in the cassette 12. Therefore, a construction is also possible in which when the number of the remaining medicines has fallen below a value (set value) set in advance, it is determined that filling is required and a cassette number of an object that requires the filling is displayed at the portable terminal 3. With this construction, it becomes possible to automatically inform the person preparing the medicine which cassette 12 needs to be filled with a medicine. In this case, it is preferable that multiple set values are provided, division into multiple areas is performed with reference to respective set values, and a display form is changed in accordance with which area the number of the remaining medicines belongs to.

It should be noted here that in the embodiment described above, it is possible to display filling records and error histories in a list on the display device of the main server 1, but it is also possible to display them on another display means such as a display device of the web server or the portable terminal.

Also, in the embodiment described above, functions are divided among the main server 1 and the web server 2 and management of the portable terminal 3 is performed at the web server 2 but all functions may be assigned to the main server 1 when there is no problem concerning a processing load. Further, the present invention is not limited to the portable terminal 3 controlled by the web server and any other control equipment may be used instead so long as it is capable of controlling multiple portable terminals 3.

BRIEF DESCRIPTION OF THE DRAWINGS

FIG. 9 is a diagram showing an error information list-display screen that is displayable on a display device of a main server of FIG. 1; and FIG. 10 is a diagram showing a filling record list-display screen that is displayable on the display device of the main server of FIG. 1.

DESCRIPTION OF REFERENCE NUMERALS

Figure 1:
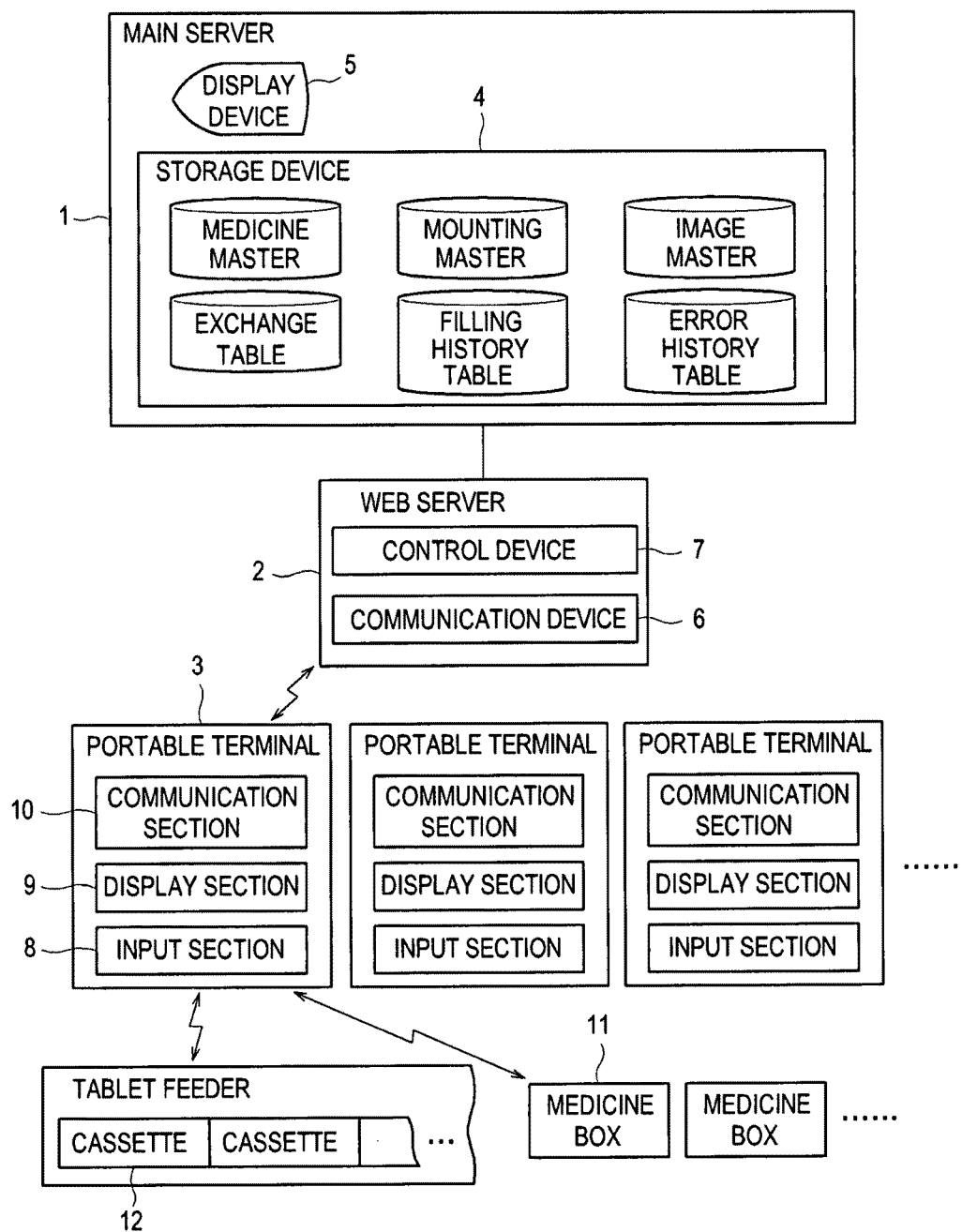
FIG. 1 is a block diagram showing the outline of a system for supporting a medicine filling operation according to an embodiment of the present invention.
Figure 2:
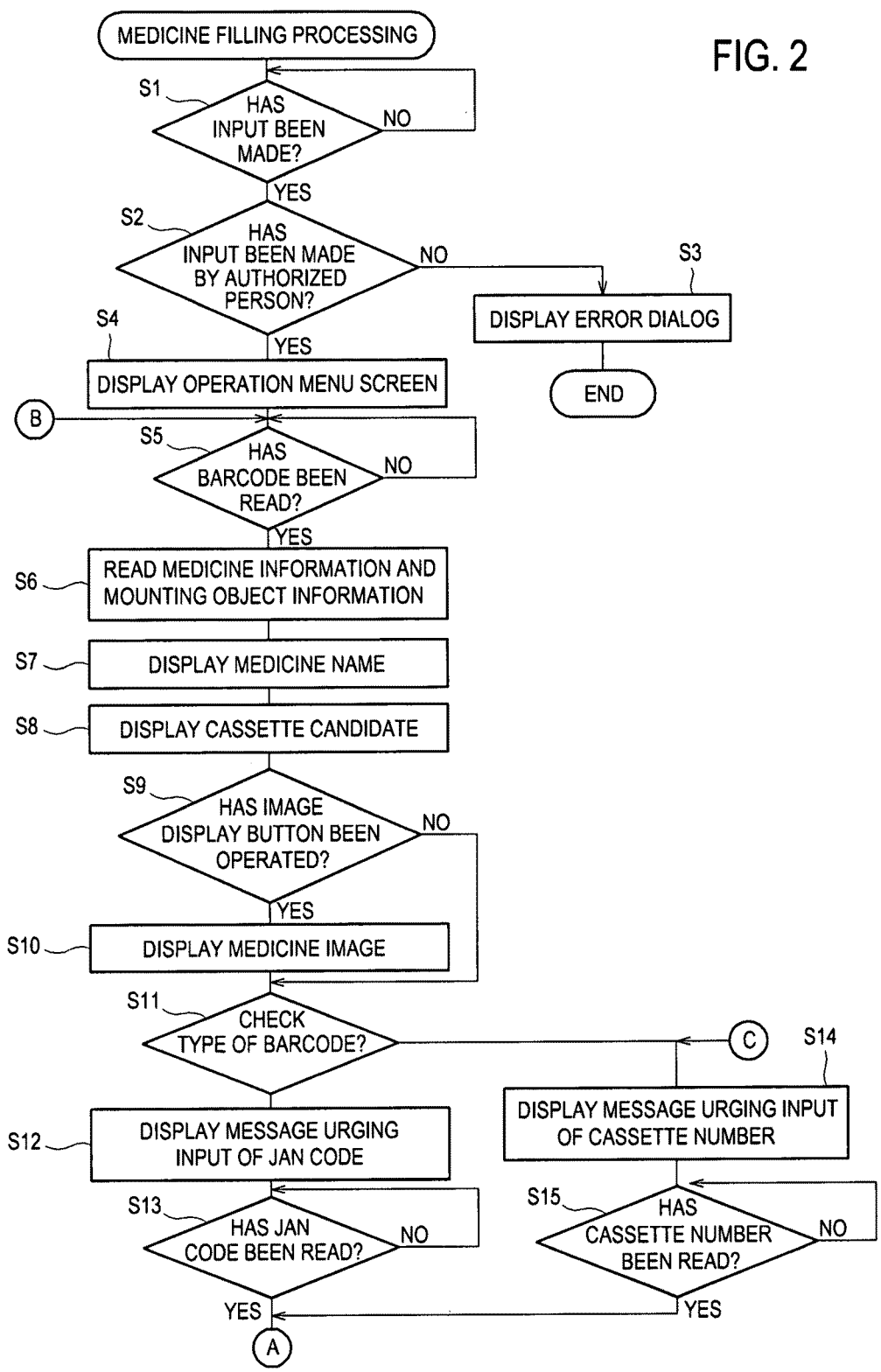
FIG. 2 is a flowchart showing the contents of medicine filling processing in the system for supporting a medicine filling operation shown in FIG. 1.
Figure 3:
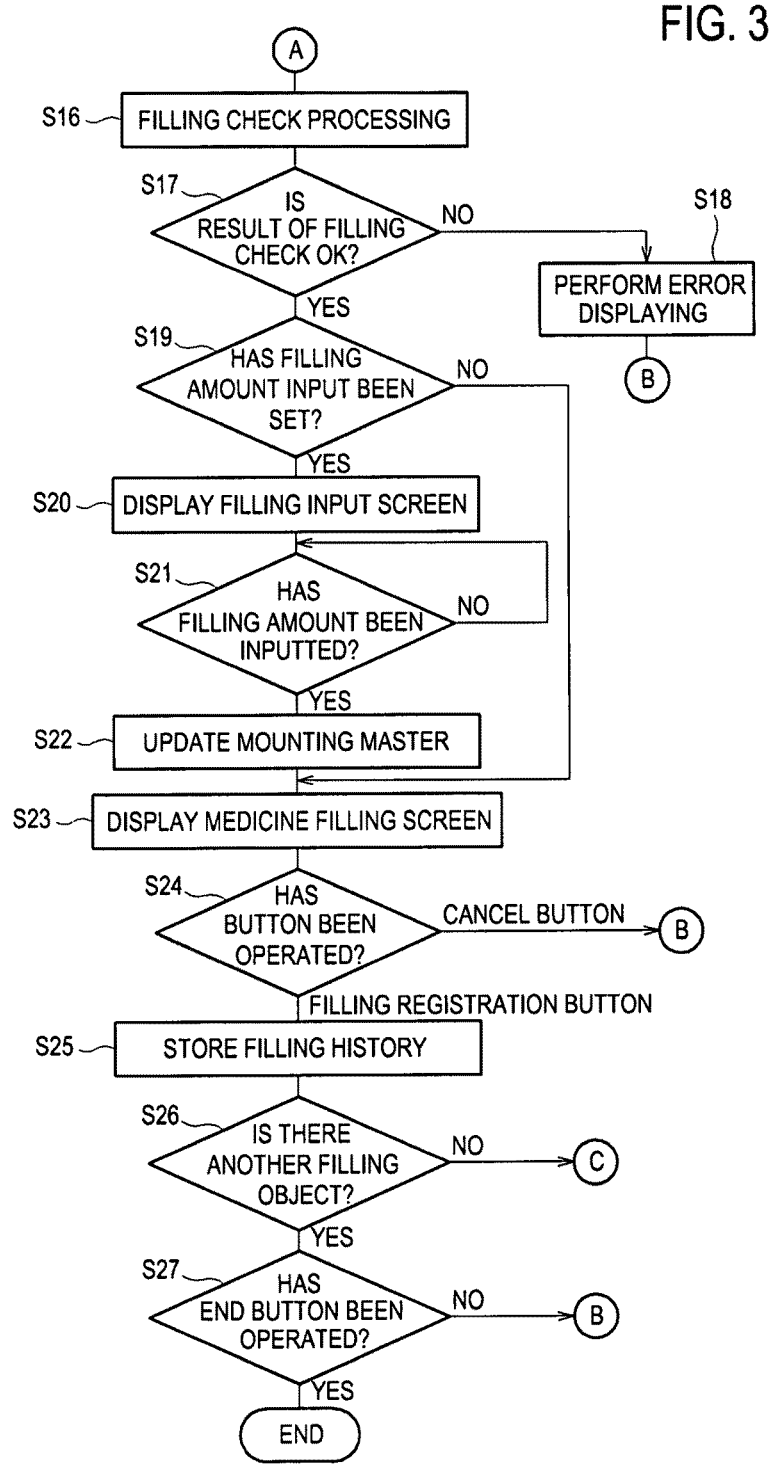
FIG. 3 is a flowchart showing the contents of the medicine filling processing in the system for supporting a medicine filling operation shown in FIG. 1.
Figure 4:
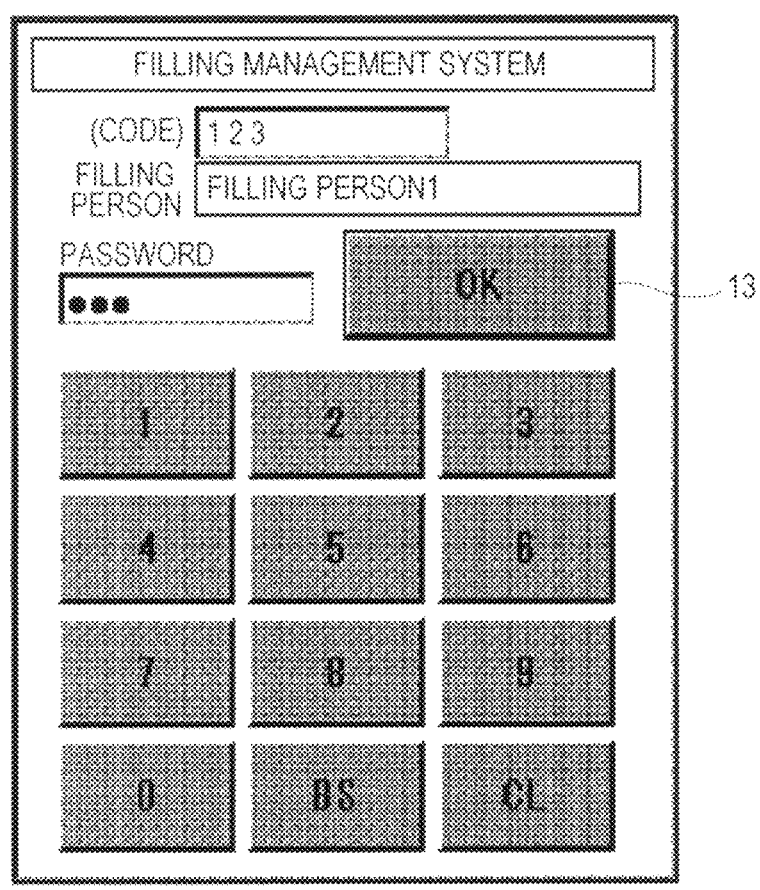
FIG. 4 is a diagram showing an initial screen displayed at each portable terminal in FIG. 1.
Figure 5:
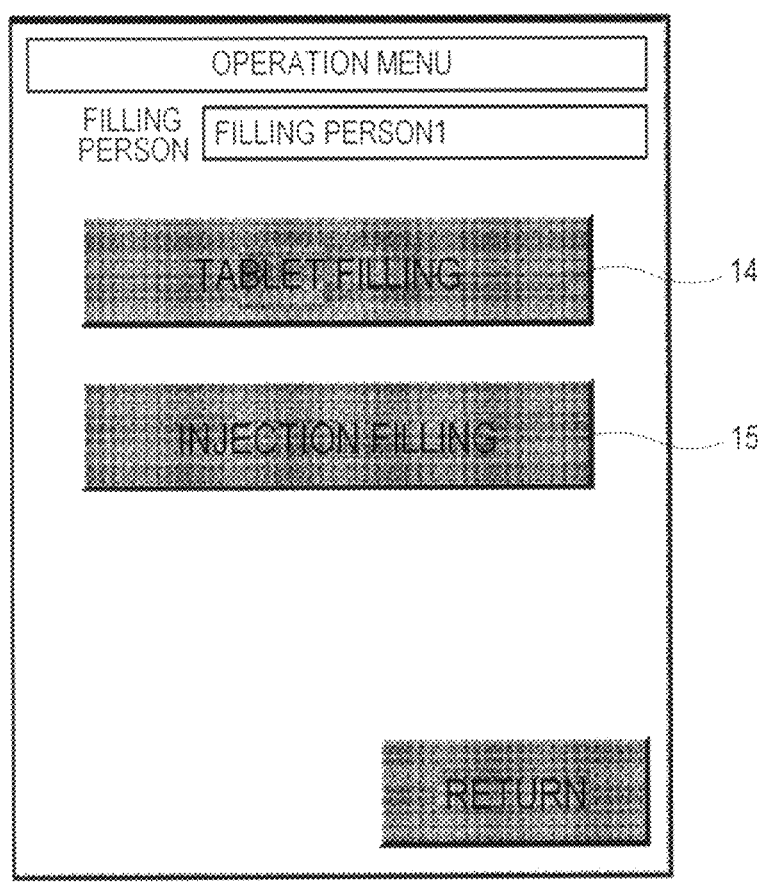
FIG. 5 is a diagram showing an operation menu screen displayed at the portable terminal in FIG. 1.
Figure 6:
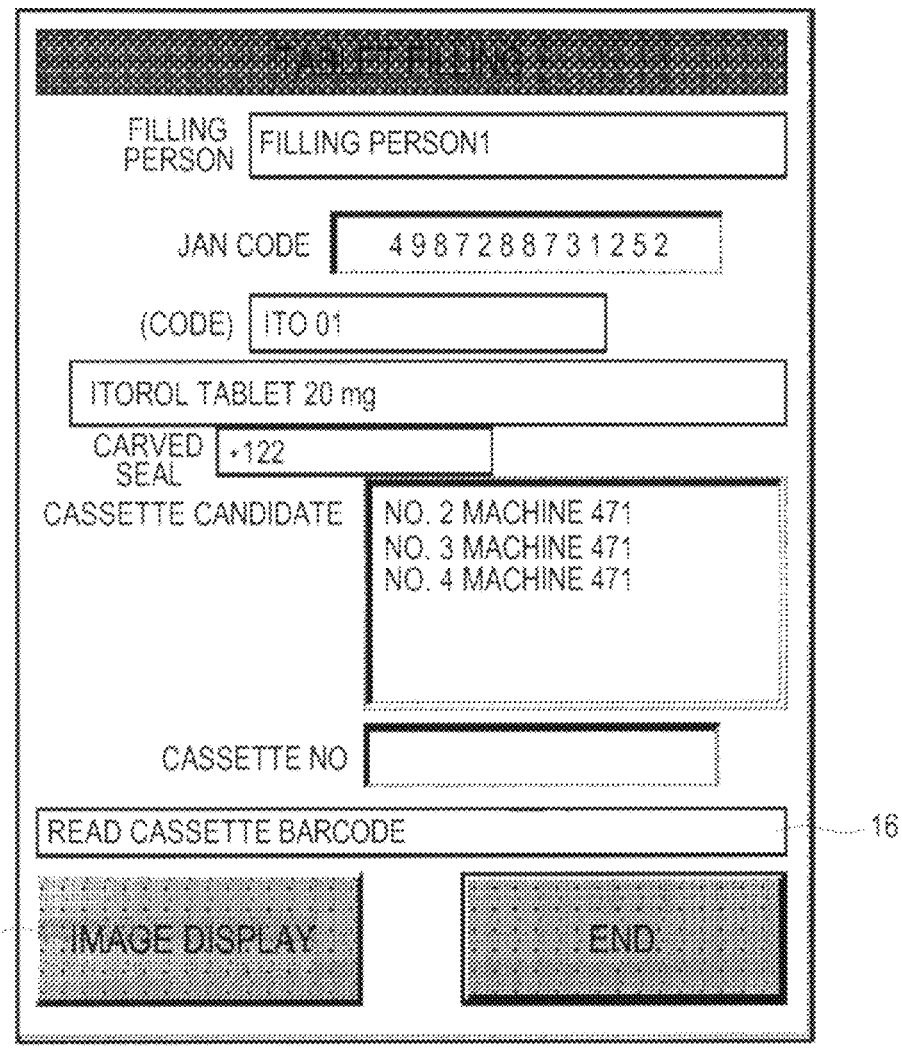
FIG. 6 is a diagram showing a tablet filling screen displayed at the portable terminal in FIG. 1.
Figure 7:
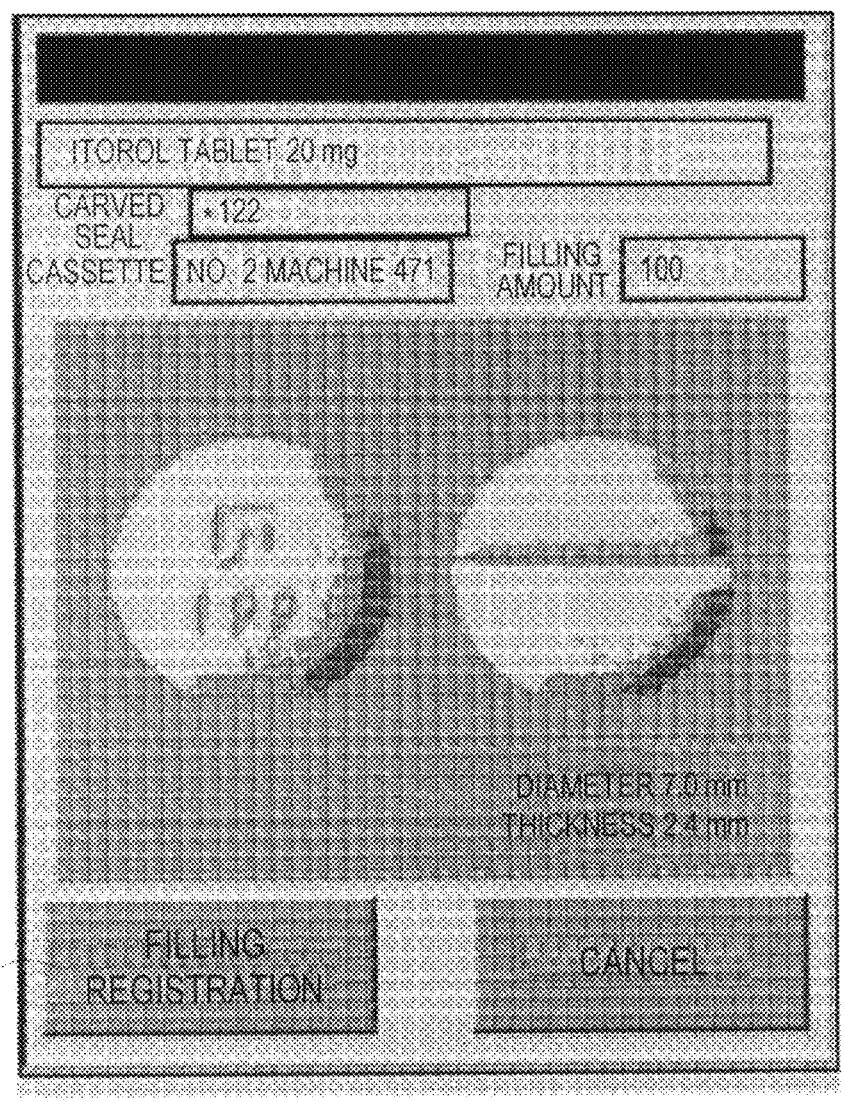
FIG. 7 is a diagram showing an image display screen displayed after an image display button has been operated in the screen of FIG. 6.
Figure 8:
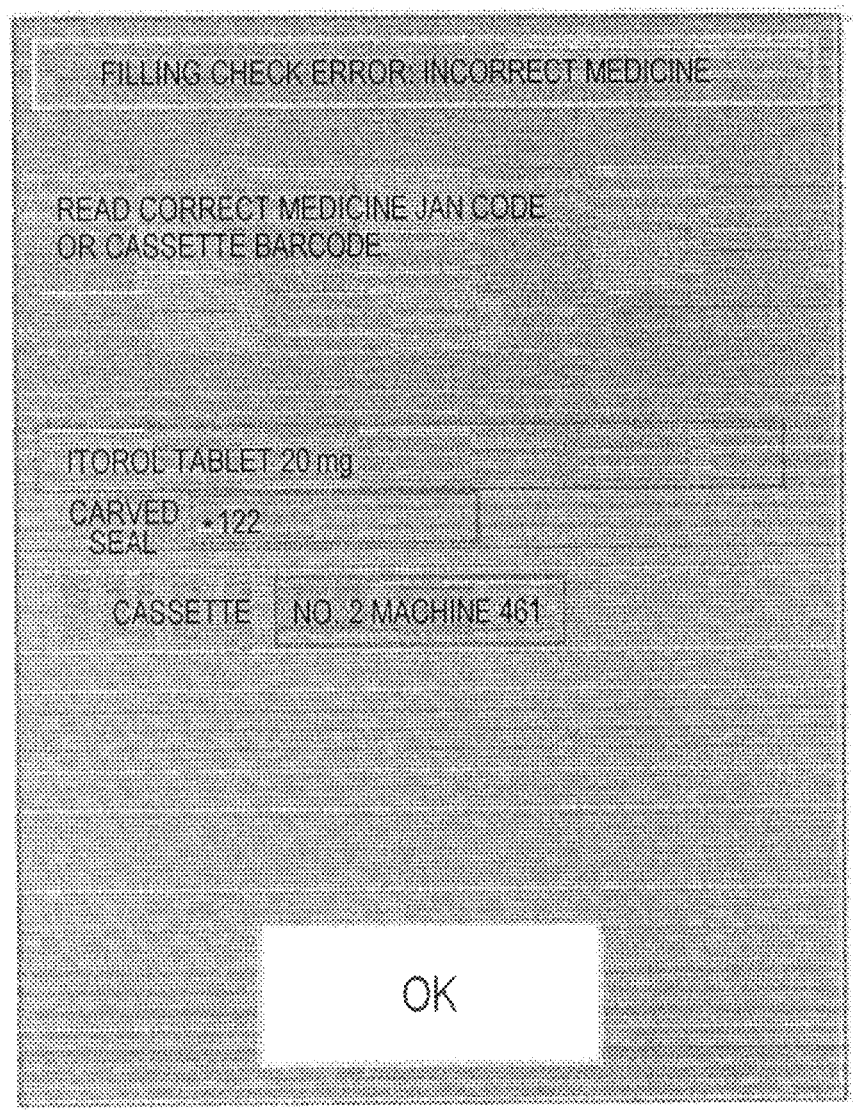
FIG. 8 is a diagram showing a check error display screen displayed at the portable terminal of FIG. 1.

1 . . . main server
2 . . . web server
3 . . . portable terminal
4 . . . storage device
5 . . . display device
6 . . . communication device
7 . . . control device
8 . . . input section
9 . . . display section
10 . . . communication section
11 . . . medicine box
12 . . . cassette
13 . . . OK button
14 . . . tablet filling button
15 . . . injection filling button
16 . . . instruction field
17 . . . image display button
18 . . . filling registration button

The invention claimed is:

1. A system for resupplying a supply cassette with medicine from a supply package, the supply cassette supplying a medicine packaging operation, comprising: a plurality of handheld terminals, each including an input section adapted to accept medicine identification information and supply cassette information for alternatively inputting one of medicine identification information for identification of the medicine within the supply package and supply cassette information for identification of the supply cassette on which the supply package is to be mounted, each handheld terminal further comprising a display section, a communication section, and an image reading section, and;

a server including:
a storage device for storing a medicine master composed of medicine information associated with the medicine identification information, a mounting master composed of supply cassette information associated with the supply cassette identification information, an exchange table for associating the medicine information and the supply cassette information with each other, and an image master composed of image information concerning the medicine;
a communication device adapted to receive the medicine identification information and the supply cassette information for alternatively receiving one of the medicine identification information and the supply cassette identification information inputted with the input section of one of the plurality of handheld terminals via the communication section; and
a control device for judging whether the medicine within the supply package and the supply cassette on which the supply cassette is to be mounted correspond to each other based on one of the medicine identification information and the supply cassette identification information received by the communication device and based on the medicine master, the mounting master, and the exchange table stored in the storage device,
wherein the image reading section receives the image information stored in the storage device via the communication section and the communication device and enables display thereof on the display section under a state where the medicine information is displayed on the display section,
wherein the storage device stores the exchange table in which one medicine is associated with a plurality of supply cassettes,
wherein, when one of the medicine identification information and the supply cassette identification information is received by the communication device, the control device is configured to read one of the medicine identification information based on the medicine master and the supply cassette identification information based on the mounting master stored in the storage device, and to read the other of the corresponding medicine identification information and the supply cassette identification information from the exchange table, and
wherein the display section of the handheld terminal is adapted to display the medicine information and the supply cassette information read by the control device and received via the communication device and the communication section.

2. The system of claim 1, wherein:
when one of the medicine identification information and the supply cassette identification information has been received by the communication device, the control device reads a corresponding one of the information based on the medicine master or the mounting master stored in the storage device and reads the other remaining one of the information associated with the read information based on the exchange table; and
the display section of the handheld terminal is adapted to display the medicine information and the supply cassette information read by the control device and received via the communication device and the communication section.

3. The system of claim 1, wherein:
the control device reads one of the medicine information and the supply cassette information stored on the exchange table in the storage device based on the one of medicine identification information and the supply cassette identification information received via the communication section and the communication device and sends the read information to the communication section of the handheld terminal via the communication device; and
when the medicine information is displayed on the display section of the handheld terminal, a plurality of corresponding supply cassettes are displayed together with the medicine information.

4. The system of claim 1, wherein the control device calculates a remaining amount of the medicine on each supply cassette based on a filling amount of the medicine into the supply cassette and a delivery amount of the medicine from the supply cassette, determines whether or not filling of the medicine is required based on the calculated remaining amount of the medicine, and displays corresponding supply cassette information on the display section of the handheld terminal when it has been determined that the filling is required.

5. The system of claim 1, wherein the control device stores a filling record together with a filling person name in the storage device based on a filling completion signal from the handheld terminal.

6. The system of claim 1, wherein when there is an error in information inputted with the input section of the handheld terminal, the control device stores an error record in the storage device and causes the display section of the handheld terminal to display error information based on the error record.

7. The system of claim 1, wherein the control device is constructed using a web server.

8. The system of claim 7, wherein:
the storage device is installed at a main server; and
the web server is installed in each unit of the plurality of handheld terminals that are collectively used.

* * * * *